United States Patent [19]
Brekhman et al.

[11] Patent Number: 4,808,574
[45] Date of Patent: Feb. 28, 1989

[54] COMPOSITION INHIBITING PATHOLOGICAL ADDICTION TO ALCOHOL

[75] Inventors: Izrail I. Brekhman; Alexandr E. Bulanov; Mira I. Polozhentseva, all of Vladivostok; Levan A. Mudzhiri, Tbilisi; Gia G. Alkhazashvili, Tbilisi; Elena I. Kalatozishvili, Tbilisi; Igor V. Dardymov, Vladivostok; Gennady N. Bezdetko, Vladivostok; Eleonora I. Khasina, Vladivostok, all of U.S.S.R.

[73] Assignees: Nauchno-Issledovatelsky Institut Sadovodstva, Akademii Nauk; Vinogradarstva I Vinodelia, Tbilisi; Institut Biologii Morya Dalnevostochnogo Nauchnogo Tsentra, Vladivostok, all of U.S.S.R.

[21] Appl. No.: 937,606

[22] Filed: Dec. 3, 1986

[51] Int. Cl.$^4$ .............. A61K 31/20; A61K 45/06; A61K 31/375
[52] U.S. Cl. .................. 514/23; 514/811; 426/11; 426/15
[58] Field of Search ............ 514/811, 23; 426/11, 426/15

[56] References Cited

U.S. PATENT DOCUMENTS

| 4,027,017 | 5/1977 | Hata et al. | 514/811 |
| 4,058,601 | 11/1977 | Hata et al. | 514/811 |
| 4,115,576 | 9/1978 | Penn | 514/811 |
| 4,318,927 | 3/1982 | Marshall | 426/11 |
| 4,593,020 | 6/1986 | Guinot | 514/811 |
| 4,596,825 | 6/1986 | Suda et al. | 514/811 |
| 4,703,045 | 10/1987 | Guinot | 514/811 |

FOREIGN PATENT DOCUMENTS

EP19423  11/1980  European Pat. Off. .
2340725  9/1977  France .

Primary Examiner—Ronald W. Griffin
Attorney, Agent, or Firm—Burgess, Ryan & Wayne

[57] ABSTRACT

The present invention relates to compositions inhibiting the development of a pathological addiction to alcohol. The composition according to the present invention consists of the following ingredients, mg/kg:

| leukoanthocyanes | 219–270 |
| catechins | 153–187 |
| flavonols | 81–99 |
| lignin | 68–83 |
| reducing sugars | 216–264 |
| pectin | 18–22 |
| free aminoacids | 27–33 |
| organic acids | 36–44 |
| sterols | 4.5–5.5 |
| methylsterols | 1.35–1.65 |
| dimethylsterols | 1.98–2.42 |
| lignans | 13.5–16.5 |
| lignan glycosides | 9–11 |
| phenolic acids | 13.5–16.5 |
| phenolic aldehydes | 4.5–5.5 |
| alkylferulates | 4.5–5.5 |

9 Claims, No Drawings

COMPOSITION INHIBITING PATHOLOGICAL ADDICTION TO ALCOHOL

The present invention relates to compositions inhibiting the development of a pathological addiction to alcohol.

FIELD OF THE INVENTION

The present invention is useful in the food industry as an additive to alcoholic and alcohol-free beverages, as an agent for prevention of alcoholism and can be employed for increasing biological value of foodstuffs (confectionery, baked goods).

BACKGROUND OF THE INVENTION

Known in the art are pharmacological agents widely employed at the present time for the treatment of patients suffering from chronic alcoholism and intended for improvement of the general resistance of the organism (tonics, vitamin therapy) and formation of negative conditional reflexes in patients for alcohol. Furthermore, also widespread have become the agents reducing toxic post-effects of alcohol and its metabolites (desintoxication therapy), as well as preparation arresting abstinence syndrom. However, the above-mentioned complex of antialcoholic therapy is aimed predominantly at the treatment of clinically pronounced forms of alcoholism or bears the character of an antirecurrence therapy.

The known complex of pharmacological preparations is not intended for a broad circle of consumers of alcoholic beverages which excludes the possibility of using these preparations for a primary prophylaxis of alcoholic abuse and chronical alcoholism.

Known in the art are synthetic preparations hindering pathological influence of alcohol on a human organism upon its intake by way of lowering the level of ethanol concentration in blood. These preparations contain, as an active ingredient, at least one compound from the group of carbohydrates and polyhydric alcohols and/or at least one compound from the group of compounds consisting of a cyclic tricarboxylic acid or containing its residue, and/or at least one compound protecting the stomach and acting as a "lining" thereon, and/or at least one compound from the group of choleretics. These preparations serve as liver-protecting agents and detoxicants upon intake of ethanol; they also cure pathological phenomena caused by resorption of alcohol (cf. French Pat. No. 2,340,725).

The above-mentioned effect is attained by normalization of the ratio of oxidized forms of pyridinenucleotides to reduced nucleotides, thus ensuring realization of carbohydrate metabolism through the cycle of tricarboxylic acids. Another active principle of these compositions are compounds lowering resorption of ethanol in the gastrointestinal tract so as to achieve a synergistic effect—reduction of the level of ethanol in blood. It is obvious that in this case the effect from intake of ethanol expected by the consumer (euphoria, relaxation) is substantially lowered. Furthermore, the prior art preparations are recommended as pharmaceutical forms to be administered either prior to ethanol intake, or simultaneously therewith, or is advisable after consumption of alcohol. These compositions, however, do not comprise food additives including those incorporated in alcoholic beverages, since they noticeably change the organoleptic value of the product.

It is an object of the present invention to provide such a composition which would actively influence the negative effects of ethanol and its toxic products of oxidation in the organism by normalization of the main metabolic routes of degradation of ethanol and its metabolites.

It is another object of the present invention to provide such a composition which would be useful as an all-purpose food additive to alcoholic or alcohol-free beverages without impairing their organoleptic characteristics.

SUMMARY OF THE INVENTION

These objects are accomplished by the provision of a composition inhibiting the development of a pathological addiction to alcohol which, according to the present invention, comprises the following ingredients, mg/g:

| | |
|---|---|
| leukoanthocyanes | 219-270 |
| catechins | 153-187 |
| flavonols | 81-99 |
| lignin | 68-83 |
| reducing sugars | 216-264 |
| pectin | 18-22 |
| free aminoacids | 27-33 |
| organic acids | 36-44 |
| sterols | 4.5-5.5 |
| methylsterols | 1.35-1.65 |
| dimethylsterols | 1.98-2.42 |
| lignans | 13.5-16.5 |
| lignan glycosides | 9-11 |
| phenolic acids | 13.5-16.5 |
| phenol aldehydes | 4.5-5.5 |
| alkylferulates | 4.5-5.5. |

The composition according to the present invention comprises a combination of compounds occurring in nature. The composition has a pronounced capability of effecting processes of ethanol metabolism without switching to unfavourable routes of the organism's utilization of ethanol; as a result, the process of formation of a physical dependence on alcohol is delayed, the level of its consumption is lowered and certain alcoholic behaviour excesses disappear. Furthermore, the composition according to the present invention is not toxic and safe after many-year consumption; it has positive organoleptic characteristics and can be useful as a food additive to alcoholic and alcohol-free beverages.

Other objects and advantages of the present invention will now become more fully apparent from the following detailed description of a composition inhibiting the development of a pathological addiction to alcohol with reference to examples illustrating its particular embodiments.

DETAILED DESCRIPTION OF THE INVENTION

The composition according to the present invention contains, as leukoanthocyanes, leukodolphinidine, leukocyanidine and leukopelargonidine. As catechins it contains (−)epigallocatechin, (±)gallocatechin, (−)epicatechin, (+)catechin and (−)epicatechingallate. As flavanols the composition according to the present invention contains kaempferol-3-monoglucoside, quercetin-3-monoglucoside, myricetin-3-monoglucoside and astragalin. A reducing sugars it contains D-glucose, D-fructose, saccharose, rafinose, arabinose, xylose. As free amonoacids the composition according to the present invention contains lysine, histidine, arginine, aspartic acid, threonine, serine, glutamic acid, proline, glycine, alanine, cystine, valine, methionine, isoleucine, leucine, tyrosine and phenylalanine. As organic acids it contains tartaric acid, malic acid, citric acid, ascorbic acid, α-ketoglutaric acid, fumaric acid, galacturonic acid, glyceric acid, glycolic acid, glycouronic acid, oxalic acid, succinic acid, shikimic acid. As sterols the composition according to the present invention contains β-cetosterol, stigmasterol, kaempesterol. As methylsterols it contains obtusifoliol, citrostadienol. As dimethylsterols it incorporates α-amyrin, β-amyrin, lupeol, taraksterol, taraxasterol, germanicol. As lignans the composition according to the present invention contains oxymatairesinol, matairesinol, pinoresinol, liovyl, isolariciresinol and olivil. As lignan glycosides it contains querinol arabinoside and querinol xyloside. As phenolic acids it contains paraoxybenzoic acid, protocatechinic acid, gallic acid, vanillic acid and syringic phenolic acids. As phenolic aldehydes the composition according to the present invention contains vanilline, syringic aldehyde, sinapic aldehyde and coniferyl aldehyde. As alkylferulates it contains alkyl esters of ferulic acid with the alcohol moiety being represented by octadecanol, eicosanol, docosanol, tetracosanol, hexacosanol.

The above-mentioned composition of the hereinbefore-listed ingredients can be also obtained in the form of naturally-occurring complexes of biologically active substances of the vegetable origin.

The above-mentioned composition of the hereinbefore-listed ingredients is soluble in water, ethanol and aqueous alcoholic solutions.

The composition according to the present invention has a low toxicity: $LD_{50}$ is 36.5 ml per 1,000 g of bodymass of a rat.

We have carried out pharmacological studies of the effect of the composition according to the present invention on processes of ethanol consumption and on the formation of a physical dependence of animals and human beings.

Under conditions of a chronical experiment (15 weeks) on mature male rats of Wistar line the level of ethanol consumption was studied under the conditions of free choice between water and 15% ethanol. Prior thereto the rats were tested for resistance to ethanol by the "side posture" procedure upon an intraperitoneal administration of a 25% ethanol at the rate of 4.5 g/kg of the bodymass of the animals. In the experiment rats with similar characteristics of a high tolerance towards ethanol were used. Later on the animals were placed into cages with calibrated drinking bowls under conditions of free choice between 15% ethanol and water, and the daily consumption of the liquids was recorded.

The control group was composed of animals (12 rats) that consumed 15% ethanol.

In the test group (12 rats) the composition according to the present invention was added to 15% ethanol in the drinking bowl in the amount of 1 ml per 50 ml of 15% ethanol. After 13 weeks of active alcoholization the animals were deprived of the access to alcohol for 10 days (deprivation period) and then the amount of consumed solutions was recorded again. The experimental data are shown in Table 1.

In the group of control animals the deprivation period proceeded with abstinence phenomena which were manifested by a changed behaviour of the animals, the signs of tremor were recorded, a moderate dishevelling of hair was noted. At the same time, in the control group no signals of abstinence were observed.

The character of consumption of 15% ethanol under free choice conditions in the control group was different from that of consumption of 15% ethanol with the composition according to the present invention in the test group. Beginning from the 8-th week a clearly pronounced trend towards reduction of ethanol consumption in combination with the composition according to the present invention was observed and after deprivation this difference was exceeding 100%. An important indicator of a formed physical dependence on ethanol in the control group was an increased rate of ethanol consumption after a 10-days' deprivation by 12%. In the test group the consumption of ethanol in combination with the composition according to the present invention after deprivation remained at the same level.

Addition, to 15% ethanol, of the composition according to the present invention under conditions of a longtime forced alcoholization (38 months) with the absence of water in the food diet has resulted in a substantial redistribution of animals in groups of alochol consumption (Table 2).

The conditions of this experiment contemplated an individual control of consumption of test solutions in groups of animals; among the rats administered with alcohol incorporating the composition according to the present invention the number of heavily-drinking animals was certainly smaller.

TABLE 1

Effect of the composition according to the present invention on the amount of consumed 15% ethanol on a daily basis (in ml/kg of 1 animal's bodyweight) under free choice conditions

| | | Statistical parameter | Time of consumption (in weeks) | | | | | | | | | | | | | | |
|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | | 15 |
| | 1 | 2 | 3 | 4 | 5 | 6 | 7 | 8 | 9 | 10 | 11 | 12 | 13 | 14 | 15 | | 17 |
| 1. | Amount of consumed 15% ethanol (control group) | $M \pm m$ | 28.9 1.86 | 20.1 1.18 | 22.5 2.29 | 26.6 2.05 | 28.3 1.86 | 25.6 1.97 | 27.5 2.32 | 26.8 1.33 | 24.0 2.06 | 28.2 2.25 | 29.7 1.76 | 29.4 3.44 | 24.7 1.29 | Deprivation 10 days | 29.4 3.12 |
| 2. | Amount of consumed 15% ethanol with addition of the composition of this invention (1 ml per 50 ml of ethanol) | $M \pm m$ p | 33.8 3.88 0.05 | 32.2 4.09 0.05 | 37.0 2.93 0.01 | 34.0 3.11 0.2 | 25.9 2.53 0.1 | 26.6 2.26 — | 29.8 1.3 — | 15.3 1.49 0.01 | 18.9 1.36 0.001 | 22.0 2.17 0.001 | 22.0 1.66 0.2 | 20.0 2.42 0.1 | 13.0 2.12 0.05 | | 13.0 2.41 0.00 |

TABLE 2

Effect of the composition according to the present invention on distribution of rats according to the rate of consumption of a 15% ethanol (in percent) (forced alcoholization)

| Groups of animals | Alcoholization time* | | |
|---|---|---|---|
| | 3 months | 6 months | 8 months |
| Low-drinking (20–60 ml per 1,000 g of the bodymass) | 26/45 | 73/76 | 67/79 |
| Medium-drinking (60–80 ml per 1,000 g of the bodymass) | 31/12 | 22/21 | 21/15 |
| Heavily-drinking (above 80 ml per 1,000 g of the bodymass) | 43/13 | 5/3 | 12/6 |

*NOTE: in the numerator - consumption of a 15% ethanol, in the denominator - consumption of a 15% ethanol with the addition of a composition according to the present invention.

To avoid possible organoleptic effect of the composition according to the present invention on the level of ethanol consumption under free-choice conditions parallel experiments have been carried out where the composition was introduced intragastrically, not into the test solution. The test results turned to be identical irrespective of the routes of administration of the composition according to the present invention.

The gas-liquid chromatography method was used to determine the amount of ethanol in blood of animals of the test and control groups that were given the test solution for the period of 3 months. 90 minutes prior to slaughtering the animals they were intraperitoneally administered with a 25% ethanol (control group) and a 25% ethanol in combination with the composition according to the present invention in the ratio of 1:50 (test group).

The test results (Table 3) point to an essential increase (by more than 4 times) of ethanol in the blood of animals that were previously administered for a long time with the composition according to the present invention.

The rate of elimination of ethanol from blood depend, first of all, on activity of alcoholdehydrogenase (ADG) which has been studied against the background of an acute and chronic alcoholic intoxication. Upon a single-time intraperitoneal administration, to animals, of a 15% ethanol in the dose of 4.5 g/kg of the bodymass, 30 minutes thereafter the activity of alcoholdehydrogenase is 8.51 mM/min/l relative to the intact group; the composition additive according to the present invention inhibits activity of enzymes in the presence of ethanol which is 5.86 mM/min/l.

TABLE 3

Effect of the composition according to the present invention on elimination of ethanol after the addition of a 25% ethanol 4.5 g/kg of the animals' bodyweight

| | Experiment | Statistical parameter | Content of ethanol in blood, % |
|---|---|---|---|
| 1. | Digested content (introduction of a 25% ethanol) 7 | M ± m | 0.72 ± 0.14 |
| 2. | 3-months' consumption of a 15% ethanol (introduction of 25% ethanol) 14 | M ± m<br>p | 1.0 ± 0.14<br>0.2 |
| 3. | 3-months' consumption of a 15% ethanol in combination with the composition of the present invention (administration of 25% ethanol) 11 | M ± m<br>p | 2.52 ± 0.57<br>0.01 |
| 4. | 3-months' consumption of a 15% ethanol in combination with the composition of this invention (administration of 25% ethanol + composition), 1:50 11 | M ± m<br>p | 4.26 ± 0.78<br>0.001 |

In chronical experiments upon introduction of ethanol (passive alcoholization) over the period of 1.5 months of a daily administration of 15% ethanol and ethanol in combination with the composition according to the present invention in the test dose of 1 g/kg the data have been obtained which prove the results of the previous experiment (see Table 4).

Under conditions of free choice between 15% ethanol and water (control group) and between a 15% ethanol with the composition according to the present invention and water after 1.5 and 3 months of consumption the activity of alcoholdehydrogenase was studied prior to and after deprivation. The results thus obtained are shown in Table 5.

Therefore, the composition additive according to the present invention decelerates oxidation of ethanol in the liver by inhibiting activity of alcoholdehydrogenase.

Observations were carried out to study the lipoid and carbohydrate metabolism in animals upon administration of the composition according to the present invention against the background of a 3- and 6-months' alcoholization.

TABLE 4

Activity of alcoholdehydrogenase in blood serum and liver upon administration of a 15% ethanol in combination with the composition according to the present invention orally for 1.5 months

| | Activity of alcohol-dehydrogenase in blood serum by the Skursky method mM/min/l | Activity of alcohol-dehydrogenase according to Bonischoen method | | Ethanol in blood μM/ml |
|---|---|---|---|---|
| | | serum mM/min/l | liver mM/min/l | |
| 1. 15% ethanol | 3.1 ± 1.17 | 3.15 ± 0.14 | 47.02 ± 1.91 | 16.21 ± 1.4 |
| 2. 15% ethanol + composition of this invention | 2.63 ± 0.49 | 2.86 ± 0.05 | 37.4 ± 1.61 | 21.87 ± 2.5 |
| 3. Composition of this invention (aqueous solution 1:50) | 2.76 ± 0.33 | 2.21 ± 0.05 | 34.39 ± 2.6 | 4.32 ± 0.4 |

TABLE 4-continued

Activity of alcoholdehydrogenase in blood serum and liver
upon administration of a 15% ethanol in combination
with the composition according to the present invention orally for 1.5 months

|   | | Activity of alcohol-dehydrogenase in blood serum by the Skursky method mM/min/l | Activity of alcohol-dehydrogenase according to Bonischoen method | | Ethanol in blood μM/ml |
|---|---|---|---|---|---|
|   | | | serum mM/min/l | liver mM/min/l | |
| 4. | Physiological solution | 2.51 ± 0.29 | 2.51 ± 0.06 | 40.5 ± 3.29 | 4.9 ± 0.6 |
| 5. | Intact | 2.6 ± 0.33 | 2.46 ± 0.09 | 40.51 ± 1.3 | 4.14 ± 0.3 |

TABLE 5

Activity of alcoholdehydrogenase at a free choice of the test solutions

|   |   | Activity of alcohol-dehydrogenase, mM/min/l | | | |
|---|---|---|---|---|---|
|   |   | 1.5 months of consumption | | 3 months of consumption | |
|   |   | prior to deprivation | after deprivation | prior to deprivation | after deprivation |
| 1. | 15% ethanol | 2.7 ± 0.26 | 3.61 ± 0.48 | 2.64 ± 0.27 | 4.3 ± 0.63 |
| 2. | 15% ethanol + composition of this invention | 1.87 ± 0.22 | 3.35 ± 0.44 | 3.95 ± 0.66 | 2.63 ± 0.49 |
| 3. | Intact | 4.33 ± 1.08 | 4.79 ± 0.64 | 2.2 ± 0.28 | 3.08 ± 0.58 |

To this end, over the period of 3 and 6 months the rats were intragastrically administered with 2 ml of the hereinbelow-specified solutions per 100 g of the body-mass. In the control: Group 1—distilled water; Group II—15% ethanol; Group III—15% ethanol containing a 5% composition according to the present invention; Group IV—aqueous solution of the composition according to the prevent invention.

The results thus obtained are shown in Tables 6, 7, 8 and 9 hereinbelow.

Then we have carried out pharmacological tests of the composition according to the present invention as an agent for improving general resistance of the organism. For this purpose the effect of the composition according to the present invention on the heat-resistance of rats has been studied.

(I) Overheating of nondescript female rats (60 animals) is effected by irradiation with an UHF-field by means of an instrument for a microwave therapy with the frequency of 2,375 mHz–17 mA for 10 days once a day over the period of 4 days. The test composition is administered in the dose of 2.5 ml/kg (intragastrically in all series of experiments) for 5 days before the beginning of irradiation and, on the day of experiment, one hour before irradiation. The death rate of rats is assessed after a 4-times' irradiation.

It has been found that during one day after the last irradiation in the control group 22% of the animals died, whereas among the rats administered with the composition according to the present invention the death rate was 11% ($p<0.01$).

(2) Overheating of male rats of the Wistar line is effected in a thermostatted cabinet at the temperature of 43° C. The test composition in the dose of 2.5 ml/kg is administered for the preventive purposes over the period of 20 days. The rectal temperature and death rate of the animals are assessed.

It has been found that in the control group 76% of the animals (28 animals out of 37) died, while against the background of the composition according to the present invention 56% of the rats died (22 rats out of 39; $p<0.001$). The composition provided no effect on the rectal temperature.

(3) Under the same conditions of overheating of male rats of the Wistar line the composition according to the present invention is administered prophylactically over 48 days in the dose of 1 ml/kg.

It has been found that in the control group 54% of rats (30 animals out of 55) died, while upon overheating against the background of a long-time administration of the composition according to the present invention the death rate was 42% (24 rats out of 57; $p<0.001$).

TABLE 6

Variation of the content of neutral lipoids in the liver of rats fed with the solutions
for 3 months (in % of the total lipoids, M ± m)

|   | Groups of animals | | | | |
|---|---|---|---|---|---|
|   | I control | II distillate | III aqueous solution of the composition of this invention | IV 15% ethanol + composition of this invention | V 15% ethanol |
| Cholesterol esters | 14,5 ± 1.10 | 14.5 ± 0.49 | 12.5 ± 0.93[1] | 12.5 ± 0.48[1] | 15.0 ± 1.21 |
| % of variation |  | 100 | 86 | 86 | 103 |
| Triglycerides | 13.6 ± 0.55 | 17.2 ± 1.11[2] | 20.1 + 0.84[3] | 20.6 + 1.77[3] | 20.1 + 1.04[3] |
| % of variation |  | 127 | 148 | 151 | 148 |
| Free fat acids | 12.8 ± 1.60 | 12.8 ± 0.48 | 12.3 ± 0.50 | 11.5 ± 0.53 | 10.6 ± 0.92[1] |
| % of variation |  | 100 | 96 | 90 | 83 |
| Cholesterol | 16.6 ± 0.9 | 17.2 ± 0.63 | 16.1 ± 0.91 | 14.2 ± 0.67[1] | 15.3 ± 1.22 |
| % of variation |  | 104 | 97 | 86 | 92 |

TABLE 6-continued

Variation of the content of neutral lipoids in the liver of rats fed with the solutions for 3 months (in % of the total lipoids, M ± m)

| | | | Groups of animals | | |
|---|---|---|---|---|---|
| | I control | II distillate | III aqueous solution of the composition of this invention | IV 15% ethanol + composition of this invention | V 15% ethanol |
| Residual fraction | 32.5 ± 1.05 | 38.3 ± 0.97 | 39.0 ± 1.02 | 41.2 ± 1.30 | 39.0 ± 1.00 |

[1] $p < 0.05$;
[2] $P < 0.02$;
[3] $P < 0.01$
p — probability

TABLE 7

Variation of the content of neutral lipoids in the liver of rats fed with the solutions for 6 months (in % of the total lipoids, M ± m)

| | | | Groups of animals | | |
|---|---|---|---|---|---|
| Neutral lipoids | Control | I distillate | II 15% ethanol | III 15% ethanol + composition of this invention | IV aqueous solution of the composition of the invention |
| Cholesterol esters | 16.9 ± 0.69 | 16.52 ± 0.70 | 16.62 ± 0.35 | 16.74 ± 0.27 | 15.81 ± 0.14 |
| % of variation | | 99 | 100 | 100 | 95 |
| Triglycerides | 15.16 ± 0.21 | 13.88 ± 0.12 | 18.19 ± 0.26[1] | 14.18 ± 0.22[1] | 13.64 ± 0.42[1] |
| % of variation | | 92 | 120 | 94 | 90 |
| Free fatty acids | 16.67 ± 0.48 | 17.21 ± 0.11 | 14.0 ± 0.39[1] | 17.30 ± 0.37 | 18.66 ± 0.88 |
| % of variation | | 103 | 84 | 104 | 112 |
| Cholesterol | 17.28 ± 0.26 | 17.07 ± 0.16 | 16.61 ± 0.69 | 16.72 ± 0.89 | 17.06 ± 0.19 |
| % of variation | | 99 | 96 | 97 | 99 |
| Residual fraction | 33.93 ± 0.40 | 35.38 ± 0.74 | 34.58 ± 0.47 | 35.06 ± 0.52 | 34.83 ± 0.61 |

[1] $p < 0.05$;
[2] $p < 0.02$

TABLE 8

Variation of activity of lysosomal hydrolases in the liver of rats upon consumption of ethanol and the composition of this invention for 3 months and 6 months (nanomol/ml/min, M ± m)

| | | 3 months | | 6 months | |
|---|---|---|---|---|---|
| | Groups of animals | β-glycosidase | β-galactosidase | β-glucosidase | β-galactosidase |
| | Control | 0.47 ± 0.04 | 0.33 ± 0.01 | 0.49 ± 0.05 | 0.35 ± 0.01 |
| 1. | Distillate | 0.43 ± 0.01 | 0.35 ± 0.01 | 0.54 ± 0.08 | 0.43 ± 0.02 |
| | % of variation of the control | 91 | 106 | 110 | 78 |
| II. | 15% ethanol | 0.58 ± 0.08[1] | 0.37 ± 0.04 | 0.87 ± 0.09[2] | 0.86 ± 0.06[3] |
| | % of variation of the control | 123 | 112 | 178 | 247 |
| III. | 15% ethanol + composition of this invention | 0.50 ± 0.05 | 0.35 ± 0.06 | 0.66 ± 0.08[1] | 0.26 ± 0.01 |
| | % of variation of the control | 106 | 106 | 135 | 75 |
| IV. | Aqueous solution of composition of this invention % | 0.40 ± 0.02 | 0.31 ± 0.03 | 0.38 ± 0.05 | 0.25 ± 0.01[1] |
| | of variation of the control | 85 | 94 | 78 | 70 |

[1] $p < 0.05$;
[2] $p < 0.01$;
[3] $p < 0.001$

TABLE 9

Variation of the content of carbohydrate-containing biopolymers in the liver of rats fed with ethanol and with the composition of the invention for 3 months and 6 months (mg %, M ± m)

| Groups of animals | 3 months | | 6 months | |
|---|---|---|---|---|
| | Hexoses | Hexosamines | Hexoses | Hexosamines |
| 1. Control | 26.68 ± 1.54 | 32.53 ± 2.37 | 26.26 + 1.43 | 49.00 ± 1.76 |
| 2. Distillate | 18.67 ± 1.12[1] | 29.60 ± 2.52 | 20.45 ± 1.72 | 68.53 ± 6.97[2] |
| % of variation of the control | 70 | 91 | 78 | 140 |
| 3. Aqueous solution | 33.35 ± 2.73[1] | 36.02 ± 1.47 | 28.91 ± 1.34 | 102.43 ± 7.63[3] |

TABLE 9-continued

Variation of the content of carbohydrate-containing biopolymers in the liver of rats fed with ethanol and with the composition of the invention for 3 months and 6 months (mg %, M ± m)

| Groups of animals | 3 months | | 6 months | |
|---|---|---|---|---|
| | Hexoses | Hexosamines | Hexoses | Hexosamines |
| of the composition of this invention | | | | |
| % of variation of the control | 125 | 111 | 110 | 209 |
| 4. 15% ethanol + composition of this invention | 18.43 ± 1.27[1] | 28.10 ± 2.65 | 19.71 ± 1.10[1] | 84.72 + 4.21[3] |
| % of variation of the control | 69 | 86 | 75 | 173 |
| 5. 15% ethanol | 16.67 ± 1.22[1] | 25.84 ± 1.77[1] | 16.32 ± 1.00[2] | 30.22 ± 5.41[2] |
| % of variation of the control | 62 | 79 | 62 | 62 |

[1] $p < 0.05$;
[2] $p < 0.01$;
[3] $p < 0.001$ (4) Overheating of male rats of the Wistar line was effected in much the same manner. The test composition was administered in the dose of 1 ml/kg 50 minutes prior to overheating. The overheating duration is 40 minutes and 2 hours. The animals were killed by decapitation. Tested were: the content of glycogen (herein and in other cases—by the Zeifter method); activity of hexokinase and glucose-6-phosphatedehydrogenase (herein and in other cases—by the formation of nicotinamidedinucleotidephosphoric acid (NADPxH).

It has been found that in overheating of the rats for 40 minutes the composition inhibited the drop of the content of glycogen, as well as of the activity of hexokinase and glucoso-6-phosphatedehydrogenase in the liver (see Table 10 hereinbelow).

Upon overheating for 2 hours the test composition provided no effect on the level of the studied parameters.

Overcooling of male rats of the Wistar line was caused by placing the animals into a refrigerator chamber at a temperature of 5° C. for 1 and 2 hours. The composition according to the present invention was administered in the dose of 1 ml/kg 60 minutes before cooling.

It has been found that upon overcooling of rats during the first hour there is observed as decrease of glycogen stock in the liver, as well as lowering of activity of hexokinase and glucoso-6-phosphatedehydrogenase in this organ. A preliminary administration of the composition according to the present invention to the animals inhibited lowering of the studied parameters (see Table 11). Upon a 2-hours' cooling the composition according to the present invention provided no protective effect.

The effect of the composition according to the present invention on animals' resistance to a muscular fatigue has been also studied. To this end:

(1) Experiments are carried out on non-descript male mice with a mass of 28-33 g. The test composition is administered enterally by means of a probe to three groups of animals in three doses: 0.1, 0.15, 0.22 ml/20 g one hour prior to the muscular work. The control animals are carried out on an "endless rope" apparatus. The duration of mice run along a vertical downwardly moving rope till a complete exhaustion was assessed. The dose of the composition extending the duration of mice run by 33% was found by graphical plotting. Activity of the studied composition was expressed in conditional units—stimulant effect units ($SEU_{33}$).

As a result of tests it has been found that the muscular workability of mice was increasing proportional to the dose of the extract.

TABLE 10

Effect of the composition according to the present invention on variation of glycogen (mg %), hexokinase ($\mu$mol of NADPxH/min/g of the tissue), glucoso-6-phosphatedehydrogenase ($\mu$mol NADPxH/min/g of the tissue) upon overheating (45° C.)

| Group of animals | Glycogen | Hexokinase | Glucoso-6-phosphatede-hydrogenase |
|---|---|---|---|
| 40 minutes of overheating | | | |
| 1. Normal | 3,226 + 148 | 0.42 + 0.025 | 1.80 + 0.61 |
| 2. Overheating | 387 + 209 | 0.34 + 0.19 | 1.57 + 0.095 |
| | $p < 0.005$ | $p < 0.020$ | $p < 0.050$ |
| 3. Overheating + composition of the present invention | 2,968 + 121 $p < 0.030$ | 0.40 + 0.18 $p < 0.030$ | 1.71 + 0.077 $p < 0.30$ |
| 2 hours of overheating | | | |
| 1. Normal | 4,628 + 207 | 0.50 + 0.019 | 1.56 + 0.058 |
| 2. Overheating | 2,175 + 271 | 0.31 + 0.027 | 1.17 + 0.095 |
| | $p < 0.0001$ | $p < 0.0001$ | $p < 0.003$ |
| 3. Overheating + composition according to the present invention | 2,869 + 219 $p < 0.060$ | 0.29 + 0.020 | 1.04 + 0.081 | p - in comparison of Groups 1-2 and Groups 2-3 upon administration of the composition according to the present invention in the maximum dose (0.22 ml/kg) the workability increased by 41% as compared to the control (see Table 12 hereinbelow).

(2) As a model of an experimental influence swimming of rats was used (herein and in other cases—male rats of the Wistar line) at the temperature of water of 30° C. The composition according to the present invention was administered to mice in the dose of 10 ml/kg one hour prior to the swimming. The ultimate duration of swimming was assessed (i.e. swimming till exhaustion).

It has been found that the rats' swimming duration in the control was 392.6±29.0 minutes, whereas against the background of the composition according to the present invention it was 519.4±40.0 minutes, i.e. by 32% longer (p=0.023).

(3) The composition according to the present invention was administered one hour before the swimming in the dose of 1 ml/kg, whereafter the animals were allowed to swim for 15 minutes or 2 hours. The state of the animals was judged by the content of glycogen, activity of hexokinase and glucoso-6-phosphatedehydrogenase in the liver.

It has been shown that the swimming of rats for both time limits specified hereinabove caused a decrease of glycogen content in the liver and lowering of the activity of hexokinase and glucoso-6-phosphatedehydrogenase. A preliminary administration of the composition according to the present invention inhibited the decrease of the studied parameters after a 2-hours' swimming, but did not affect their level after a 15-minutes' muscular load (see Table 13).

(4) The composition according to the present invention was administered one hour before a 15-minutes' swimming. The content of cyclic adepasinemonophosphate in adrenal glands, the content of cyclic guanosinemonophosphate in adrenal glands and in the liver was determined by the radioimmune method by means of sets Ammerscham. A number of rats from the test and control groups were allowed to rest after swimming for one hour, whereafter the same characteristics were studied in them too.

The swimming of rats caused elevation of the level of cyclic adepasinemonophosphate and cyclic guanosinemonophosphate in adrenal glands, as well as reduction of the content of cyclic guanosinemonophosphate in the liver (acute stress at an energy supply at the account of glycolysis). After the animals' rest for one hour the level of cyclic adepasinemonophosphate and that of cyclic guanosinemonophosphate were turned to normal values. The composition according to the present invention provided no effect on the content of cyclic adepasinemonophosphate and cyclic guanosinemonophosphate in adrenal glands, but the biosynthesis of cyclic guanosinemonophosphate in the liver one hour after swimming came to its normal values (see Table 14 hereinbelow).

The composition according to the present invention was also studied for resistance of rats to hypokinesia which was induced by keeping animals in individual cell-cages for 2 days. The test composition was administered during the entire period of hypokinesia in the dose of 1 ml/kg twice a day.

As a result of hypokinesia a reduction of glycogen stock in the liver was observed along with a decrease of concentration of cholesterol in adrenal glands and lowering of the activity of alcoholdehydrogenase (as determined by the method suggested by Schleisinger et al., 1966). In the animals administered with the composition according to the present invention the reduction of the studied parameters after hypokinesia was less pronounced (see Table 15 hereinbelow).

We have also studied the effect produced by the composition according to the present invention on resistance of animals to different chemical factors.

(1) As a model of an injuring effect a hexenal narcosis was used. The composition according to the present invention was administered to rats in the doses of 2.5, 5.0, 10.0 ml/kg; 2 hours thereafter hexenal was administered intraperitoneally in the dose of 19.8 mg/100 g. The duration of the side posture state of the animals was assessed.

It has been found that the duration of the hexenal narcosis of the control rats was $90.6 \pm 3.9$ minutes, while against the background of the composition according to the present invention administered in the dose of 2.5 mg/kg it was $85.5 \pm 5.4$ min, in the dose of 5.0 ml/kg–$75.7 \pm 3.1$ min (83.6%, $p=0.009$), in the dose of 10.0 ml/kg–$72.9 \pm 3.7$ (80.5%, $p=0.005$) that is, the composition according to the present invention exerted an awakening dose-depending effect.

(2) In experiments on mice narcosis was caused by means of sodium thiopental in three doses: 62.5, 75.0 and 100 mg/kg intraperitoneally. The composition according to the present invention was introduced in the dose of 10.0 ml/kg two hours before the injection of thiopental. The speed of occurrence of the side posture was determined, as well as the duration of the side posture period and the death rate of the animals was assessed.

It has been found that out of the mice administered with thiopental (62.5 mg/kg) against the background of the composition according to the present invention the side posture was acquired by 22% of the animals, whereas in the control (thiopental)—100% of the mice ($p=0.001$). The duration of the side posture period in the control was 53.5 minutes, in the experiment—120 minutes ($p<0.05$).

In the group of mice administered with thiopental in the dose of 75 mg/kg 28% of the animals died, whereas in the group of rats administered with thiopental against the background of the composition according to the present invention 12.5% of the animals died ($p<0.001$). In the control group the side posture period lasted for $30.0 \pm 0.0$ minutes, whereas against the background of the composition according to the present invention—$260 \pm 0.0$ minutes ($p<0.05$). The death rate of the animals in both groups was the same.

The composition according to the present invention has been also studied for certain aspects of carbohydrate metabolism. To this end:

(1) In experiments on intact animals under conditions of a conventional feeding diet the composition according to the present invention was administered twice a day over 5 days. In this and subsequent series of experiments the concentration of glucose in blood was determined by the anthrone method, the content of glycogen in the liver—by the Zeifter method.

It has been found that a 5-days' administration of the composition according to the present invention to intact animals caused a certain increase of sugar concentrations in blood and of glycogen in the liver (see Table 16).

(2) The study of carbohydrate metabolism has been performed on rats subjected to starvation for 18 or 48 hours. The test composition was administered in the dose of 1 mg/kg 1 hour prior to slaughter of the animals. The content of sugar in blood, the level of insulin in blood serum were determined by the radioimmune method.

It has been shown that a 18-hours' starvation of rats has caused reduction of the glycemia level. The test composition inhibited reduction of the sugar content in blood (see Table 16). The rats' starvation for 48 hours has caused a certain reduction of the sugar content on blood and glycogen content in the liver. This was accompanied by a lowered concentration of insulin in blood serum.

In a preliminary 5-days' administration of the composition according to the present invention to the animals only a trend was observed towards preservation of a previous level of sugar in blood and of glycogen in the liver. In this case the content of insulin in blood was certainly higher than in the control (subjected to starvation) animals (see Table 16 hereinbelow).

(3) The effect of the composition according to the present invention on the carbohydrate metabolism was studied on rats fed with an excessive diet. The composition was administered in the dose of 1 ml/kg 1 hour before slaughter.

Under conditions of an excessive diet of the rats the studied extract provided no effect on the concentration of sugar in blood, but it certainly increased the content of glycogen in the liver and reduced the level of insulin in blood (see Table 16 hereinbelow).

We have studied antioxidation properties of the composition according to the present invention. To this end, in order to activate a peroxy oxidation of lipoids, in rats of the Wistar line (40 animals) stress was caused by suspending them by the neck skin fold for 24 hours. The test group of animals was administered once with the composition of the present invention in the dose of 1 ml/kg prior to suspending. The accumulation of lipoid peroxides in the liver was assessed by the concentration of malonic dialdehyde in this organ.

It has been found that the composition according to the present invention caused no changes in the content of malonic dialdehyde in the liver of intact rats. In the rats underwent the stress treatment the content of malonic dialdehyde in the liver increased by 6 times, whereas in the case of stress against the background of the composition according to the present invention the rate of accumulation of malonic dialdehyde was noticeably smaller (normal—$86.5 \pm 29.0$; stress—$452 \pm 20$; stress+composition according to the present invention—$296 \pm 15$; $p=0.001$).

Consequently, the composition according to the present invention possesses antioxidant properties.

We have also studied biochemical characteristics of human beings administered with the composition according to the present invention against the background of alcoholization.

Under clinical conditions the effect of the composition according to the present invention on the rate of elimination of ethanol from blood and on activity of blood alcoholdehydrogenase, as well as on activity characteristics of lysosomal hydrolases, the level of protein-combined hexosoamines and on fractions of neutral lipids was studied. The first group of patients who took part in the studies consisted of persons suffering from chronic alcoholism and subjected to a stationary treatment; the second group was composed of persons belonging to the Mongoloid race genetically intolerant to alcohol; the third group—substantially healthy Europoids who did not abuse alcohol.

TABLE 11

Effect of the composition of this invention on variation of the content of glycogen (mg %) and activity of hexokinase ($\mu$mol NADPxH/min/g of the tissue) and glucoso-6-phosphate-dehydrogenase ($\mu$mol/NADPxH/min/g of the tissue) in the liver of rats upon overcooling (5° C.)

| Group of animals | Glycogen | Hexokinase | Glucoso-6-phosphate-dehydrogenase |
|---|---|---|---|
| | 1 hour of overcooling | | |
| 1 Normal | $4109 + 195$ | $0.51 + 0.017$ | $1.62 + 0.078$ |
| 2 Overcooling | $2794 + 207$ $p < 0.0001$ | $0.41 + 0.022$ $p < 0.003$ | $1.20 + 0.101$ $p > 0.004$ |
| 3 Overcooling + composition of this invention | $p < 0.020$ | $p < 0.020$ | |
| | 2 hours of overcooling | | |
| 1 Normal | $3078 + 189$ | $0.63 + 0.017$ | $1.57 + 0.075$ |
| 2 Overcooling | $1754 + 237$ | $0.47 + 0.028$ | $1.27 + 0.103$ |
| 3 Overcooling + composition of this invention | $p < 0.001$ $1908 + 226$ | $p < 0.0001$ $0.44 + 0.022$ | $p < 0.037$ $1.41 + 0.091$ | p - in comparison of Groups 1–2 and 2–3.

TABLE 12

Stimulant effect of the composition of this invention on duration of the muscular workability of mice in an "endless rope" apparatus

| | Duration of the run of the mice | | |
|---|---|---|---|
| Group of animals | minutes | % | p |
| Physiological solution (13) | $27.0 \pm 2.1$ | 100 | |
| Composition of the invention | | | |
| 0.1 ml/20 g (10) | $30.0 + 1.8$ | 111 | 0.5 |
| 0.15 ml/20 g (11) | $32.0 + 2.8$ | 118 | 0.5 |
| 0.22 ml/20 g (15) | $38.0 + 2.7$ | 141 | 0.001 |

Note: Shown in brackets is the number of animals.

TABLE 13

Effect of the composition of this invention on the content of glycogen (mg %) and activity of hexokinase ($\mu$mol NADPxH/min/g of the tissue) and glucoso-6-phosphatedehydrogenase ($\mu$umol NADPxH/min/g of the tissue) in the liver of rats in swimming (water temperature 30–32° C.)

| Group of animals 1 | Glycogen 2 | Hexokinase 3 | Glucoso-6-phosphatede-hydrogenase 4 |
|---|---|---|---|
| | Swimming for 15 minutes | | |
| 1 Normal | $4216 + 216$ | $0.50 + 0.019$ | $1.44 + 0.068$ |
| 2 Swimming | $2993 + 278$ $p < 0.002$ | $0.31 + 0.029$ $p < 0.001$ | $1.01 + 0.094$ $p < 0.010$ |
| 3 Swimming + composition of the invention | $2902 + 202$ | $0.35 + 0.015$ | $0.98 + 0.101$ |
| | Swimming for 60 minutes | | |
| 1 Normal | $3511 + 201$ | $0.54 + 0.025$ | $1.51 + 0.075$ |
| 2 Swimming | $2633 + 163$ $p < 0.004$ | $0.37 + 0.024$ $p < 0.0001$ | $1.13 + 0.095$ $p < 0.008$ |
| 3 Swimming + composition of this invention | $3089 + 133$ $p < 0.040$ | $0.44 + 0.021$ $p < 0.040$ | $1.39 + 0.071$ $p < 0.040$ | p - in comparison of Groups 1–2 and 2–3

TABLE 14

Effect of the composition of this invention on the content of CAMP in adrenal glands, CGMP in adrenal glands and liver of rats after a muscular load and rest

| Group of animals 1 | CAMP, pmol adrenal glands 2 | CGMP, pmol adrenal glands 3 | CGMP, pmol liver 4 |
|---|---|---|---|
| 1 Intact | $8.5 + 0.55$ (7) | $0.09 + 0.01$ (7) | $0.22 + 0.67$ (7) |
| 2 Swimming 15 minutes | $17.9 + 1.8$ (7) $p < 0.05$ | $0.30 + 0.04$ (7) $p < 0.001$ | $0.14 + 0.035$ (7) |
| 3 Swimming for 15 min and rest for 1 h | $8.1 + 0.63$ (6) $p < 0.05$ | $0.18 + 0.02$ (7) $p < 0.001$ | $0.059 + 0.045$ (6) $p < 0.001$ |
| 4 Swimming | $17.3 + 1.87$ (7) | $0.25 + 0.06$ (6) | $0.25 +$ |

TABLE 14-continued

Effect of the composition of this invention on the content of CAMP in adrenal glands, CGMP in adrenal glands and liver of rats after a muscular load and rest

| Group of animals 1 | CAMP, pmol adrenal glands 2 | CGMP, pmol adrenal glands 3 | liver 4 |
|---|---|---|---|
| for 15 min and the composition of this invention | | | 0.06 (6) |
| 5 Swimming for 15 min + composition of this invention and rest for 1 hour | 9.0 + 0.65 (6) | 0.14 + 0.01 (7) $p < 0.05$ | 0.136 + 0.009 (7) $p < 0.0001$ |

TABLE 15

Effect of the composition of this invention on the content of cholesterol in adrenal glands (mg/g), the content of glycogen (mg %) and activity of alcoholdehydrogenase ($\mu$mol NADP × H/min/g of the tissue) in the liver of rats under hypokinesia (2 days)

| Group of animals 1 | Cholesterol 2 | Glycogen 3 | Alcoholdehyrogenase 4 |
|---|---|---|---|
| 1 Normal | 44 + 1.6 | 3975 + 222 | 5.04 + 0.234 |
| 2 Hypokinesia | 96 + 2.4 $p < 0.01$ | 2862 + 251 $p < 0.004$ | 5.90 + 0.250 $p < 0.02$ |
| 3 Hypokinesia + composition of this invention | $p < 0.03$ | $p < 0.04$ | $p < 0.01$ |

TABLE 16

Effect of the composition of this invention on some parameters of the carbohydrate metabolism in rats

| Group of animals 1 | Blood sugar, mg % 2 | Liver glycogen, mg % 3 | Blood insulin, $\mu$UN/ml 4 |
|---|---|---|---|
| *Normal diet of rats* | | | |
| Normal | 91.0 + 2.7 (9) | 4966 + 406 (9) | — |
| Composition of this invention | 100.5 + 1.78$^x$ (13) | 6071 + 250$^x$ (10) | — |
| *Starvation for 18 hours* | | | |
| Normal diet (10) | 106.8 + 3.7 | — | — |
| Starvation (8) | 83.8 + 2.0$^x$ | — | — |
| Starvation + 1 ml/kg of composition of this invention 30 minutes before slaughtering (10) | 106.0 + 4.2$^x$ | — | — |
| *Starvation for 40 hours* | | | |
| Normal diet (10) | 116.5 + 5.0 | 5059 + 452 | 17.56 + 1.12 |
| Starvation (10) | 86.0 + 5.0$^x$ | 495 + 257$^x$ | 9.56 + 0.69 |
| Starvation + composition of this invention | 91.0 + 5.0 | 593 + 151 | 14.5 + 1.0$^x$ |
| *Excessive diet of rats* | | | |
| Without composition of this invention (10) | 119.0 + 4.3 | 4966 + 406 | 22.8 + 2.3 |
| Composition of this invention | 122.3 + 2.7 | 6071 + 250$^x$ | 17.3 + 1.19$^x$ |

$^x p < 0.05$,
Composition of this invention is administered intragastrically in the dose of 1 ml/kg twice a day over 5 days. Shown in brackets is the number of animals.

TABLE 17

Activity of $\beta$-galactosidase in blood serum of volunteers (nanomol/ml/min, M ± m)

| No. 1 | Groups 2 | 40% ethanol Background 3 | 1 hour 4 | 2 hours 5 | 4 hours 6 | Aqueous solution of the composition of this invention background 7 | 1 hour 8 |
|---|---|---|---|---|---|---|---|
| 1 | Healthy europeoids % of variation | 5.95 ± 0.62 | 6.66 ± 0.21 112 | 19.94 ± 1.22$^3$ 335 | 35.57 ± 1.63$^3$ 598 | 5.72 ± 0.19 | 5.09 ± 0.27 89 |
| 2. | Mongoloids % of variation | 5.77 ± 0.94 | 5.92 ± 0.68 103 | 12.15 ± 0.87$^3$ 211 | 12.61 ± 0.98$^3$ 219 | 6.89 ± 0.47 | 6.30 ± 0.33 91 |
| 3. | Alcoholism suffering patients % of variation | 8.79 ± 0.67 | 21.92 ± 0.94$^3$ 249 | 7.98 ± 0.20 91 | 10.46 ± 0.91$^1$ 122 | 11.72 ± 0.72 | 11.95 ± 0.83 102 |

| No. 1 | Groups 2 | Aqueous solution of the composition of this invention 2 hours 9 | 4 hours 10 | NN 40% ethanol + composition of this invention background 11 | 1 hour 12 | 2 hours 13 | 4 hours 14 |
|---|---|---|---|---|---|---|---|
| 1 | Healthy europeoids % of variation | 4.06 ± 0.44$^1$ 71 | 6.85 ± 0.48$^1$ 120 | 5.90 ± 0.42 | 5.78 ± 0.54 98 | 6.55 ± 0.42 111 | 18.0 ± 1.6$^3$ 305 |
| 2. | Mongoloids % of variation | 6.87 ± 0.57 99 | 7.50 ± 0.44 109 | 6.33 ± 0.44 | 9.39 ± 0.71 148 | 9.23 ± 0.84 146 | 16.4 ± 1.5 259 |
| 3. | Alcoholism suffering patients % of variation | 13.94 ± 0.85 119 | 24.26 ± 1.58$^3$ 207 | 10.45 ± 0.39 | 15.15 ± 0.72$^2$ 145 | 14.00 ± 0.86$^2$ 134 | 12.8 ± 0.9$^2$ 122 |

$^1 p < 0.05$
$^2 p < 0.01$
$^3 p < 0.001$ p - in comparison of Groups 1-2 and 2-3

TABLE 18

Variation of the content of hexosamines in human blood serum (mg %), M ± m

| NN 1 | Groups of volunteers 2 | I. Healthy europeoids background 3 | 1 hour 4 | 2 hours 5 | 4 hours 6 | II Healthy mongoloids background 7 | 1 hour 8 |
|---|---|---|---|---|---|---|---|
| 1. | 40% ethanol % of variation vs. | 72.57 ± 3.55 | 66.93 ± 4.10 92 | 66.00 ± 2.51 91 | 61.20 ± 2.62 85 | 48.93 ± 3.31 | 46.40 ± 1.72 95 |

TABLE 18-continued

Variation of the content of hexosamines in human blood serum (mg %), M ± m

| NN | Groups of volunteers | | | | | | |
|---|---|---|---|---|---|---|---|
| 1 | 2 | | | | | | |
| 2. | 40% ethanol + composition of this invention | 53.33 ± 2.39 | 50.40 ± 3.85 | 42.53 ± 1.79[2] | 50.53 ± 3.27 | 84.60 ± 3.70 | 63.20 ± 1.21[3] |
| | % of variation vs. the background | | 95 | 80 | 95 | | 75 |
| 3. | Composition of this invention | 72.16 ± 4.01 | 94.13 ± 3.92 | 93.44 ± 4.04[3] | 87.52 ± 1.90[2] | 36.68 ± 3.71 | 45.21 ± 3.00[1] |
| | % of variation vs. the background | | 131 | 130 | 122 | | 127 |

| | Groups of | II Healthy mongoloids | | III. Alcoholism-suffering patients | | | |
|---|---|---|---|---|---|---|---|
| NN | volunteers | 2 hours | 4 hours | background | I hour | 2 hours | 4 hours |
| 1 | 2 | 9 | 10 | 11 | 12 | 13 | 14 |
| 1. | 40% ethanol | 48.64 ± 2.93 | 53.20 ± 3.75 | 68.30 ± 2.76 | 56.06 ± 2.81[1] | 54.64 ± 3.43[1] | 57.37 ± 3.32[1] |
| | % of variation vs. the background | 99 | 109 | | 82 | 80 | 84 |
| 2. | 40% ethanol + composition of this invention | 100.64 ± 3.70[2] | 93.33 ± 4.22 | 75.94 ± 4.41 | 73.71 ± 3.10 | 66.97 ± 5.37 | 70.42 ± 4.16 |
| | % of variation vs. the background | 119 | 110 | | 97 | 88 | 93 |
| 3. | Composition of this invention | 53.20 ± 1.52[1] | 53.20 ± 2.74[3] | 60.11 ± 4.81 | 62.27 ± 3.15 | 69.94 ± 3.00[1] | 60.23 ± 3.30 |
| | % of variation vs. the background | 149 | 149 | | 103 | 116 | 100 |

[1] $p < 0.05$
[2] $p < 0.01$
[3] $p < 0.001$

TABLE 19

Variation of the content of fractions of neutral lipoids in human blood serum of persons consumed 40% ethanol (in % of the total lipoids, M ± m)

| | | I group | | | | II group | |
|---|---|---|---|---|---|---|---|
| NN | | | I | 2 | 4 | background | I hour |
| 1 | Fractions | background | hour | hours | hours | 7 | 8 |
| 1. | Cholesterol esters | 21.72 ± 1.81 | 27.03 ± 1.32[1] | 23.06 ± 1.15 | 23.95 ± 0.90 | 26.66 ± 1.19 | 27.89 ± 1.33 |
| | % of variation | | 125 | 106 | 110 | | 105 |
| 2. | Triglycerides | 17.40 ± 0.72 | 16.53 ± 0.97 | 19.11 ± 0.75 | 19.08 ± 0.78 | 17.45 ± 0.76 | 16.63 ± 0.86 |
| | % of variation | | 95 | 110 | 110 | | 95 |
| 3. | Free fatty acids | 17.06 ± 0.65 | 16.88 ± 0.50 | 15.87 ± 0.42 | 17.24 ± 0.95 | 15.10 ± 0.47 | 16.57 ± 1.08 |
| | % of variation | | 99 | 93 | 101 | | 110 |
| 4. | Cholesterol | 19.64 ± 0.86 | 18.25 ± 0.87 | 19.04 ± 0.24 | 19.08 ± 0.48 | 18.54 ± 0.50 | 17.79 ± 0.26 |
| | % of variation | | 93 | 97 | 97 | | 96 |
| 5. | Residual combined fraction | 24.18 ± 0.52 | 24.29 ± 1.85 | 22.92 ± 0.73 | 20.65 ± 0.70 | 22.25 ± 0.31 | 21.12 ± 0.64 |

| | | II group | | III group | | | |
|---|---|---|---|---|---|---|---|
| NN | | 2 hours | 4 hours | background | I hour | 2 hours | 4 hours |
| 1 | Fractions | 9 | 10 | 11 | 12 | 13 | 14 |
| 1. | Cholesterol esters | 21.22 ± 0.54 | 29.62 ± 1.44 | 25.90 ± 2.14 | 26.47 ± 2.16 | 22.66 ± 1.05 | 25.37 ± 2.48 |
| | % of variation | 80 | 111 | | 102 | 88 | 98 |
| 2. | Triglycerides | 16.48 ± 0.71 | 19.02 ± 0.22 | 15.28 ± 1.05 | 15.40 ± 0.76 | 16.37 ± 0.69 | 15.92 ± 1.24 |
| | % of variation | 94 | 110 | | 101 | 107 | 105 |
| 3. | Free fatty acids | 18.45 ± 0.57[2] | 13.87 ± 1.15 | 15.29 ± 1.35 | 18.64 ± 47[1] | 19.29 ± 0.47[2] | 16.69 ± 1.99 |
| | % of variation | 122 | 92 | | 122 | 126 | 109 |
| 4. | Cholesterol | 20.04 ± 0.66 | 17.03 ± 0.71 | 17.94 ± 0.99 | 18.71 ± 1.74 | 21.65 ± 1.96 | 19.82 ± 0.71 |
| | % of variation | 108 | 92 | | 104 | 121 | 111 |
| 5. | Residual combined fraction | 23.75 ± 0.97 | 20.46 ± 0.93 | 25.60 ± 1.68 | 20.78 ± 0.81 | 20.03 ± 1.16 | 22.13 ± 1.29 |

[1] $p < 0.05$;
[2] $p < 0.01$
Group I - healthy europeoids;
Group II - healthy mongoloids;
Group III - alcoholism-suffering patients

TABLE 20

Variation of the content of fractions of neutral lipoids in human blood serum of patients consumed aqueous solution of the composition of this invention (in % of the total lipoids, M ± m)

| | | Group I | | | | Group II | |
|---|---|---|---|---|---|---|---|
| NN | Fractions | background | I hour | 2 hours | 4 hours | background | I hour |
| 1 | 2 | 3 | 4 | 5 | 6 | 7 | 8 |
| 1. | Cholesterol | 23.07 ± 1.47 | 22.74 ± 2.10 | 23.44 ± 0.54 | 23.10 ± 0.89 | 23.12 ± 1.32 | 21.34 ± 1.38 |

TABLE 20-continued

Variation of the content of fractions of neutral lipoids in human blood serum of patients consumed aqueous solution of the composition of this invention (in % of the total lipoids, M ± m)

| NN 1 | Fractions 2 | | | | | |
|---|---|---|---|---|---|---|
| | esters | | | | | |
| | % of variation | | 99 | 102 | 101 | 92 |
| 2. | Triglycerides | 17.24 ± 0.82 | 16.75 ± 0.67 | 20.49 ± 1.29 | 17.63 ± 0.75 | 16.79 ± 2.02 | 18.99 ± 0.47 |
| | % of variation | | 97 | 119 | 102 | | 113 |
| 3. | Free fatty acids | 16.14 ± 1.20 | 17.17 ± 0.39 | 16.85 ± 0.42 | 17.90 ± 0.63 | 17.77 ± 1.03 | 18.05 ± 0.48 |
| | % of variation | | 110 | 104 | 111 | | 102 |
| 4. | Cholesterol | 17.43 ± 1.57 | 18.69 ± 1.93 | 19.97 ± 0.54 | 17.89 ± 0.93 | 18.09 ± 0.60 | 20.33 ± 0.37 |
| | % of variation | | 107 | 115 | 103 | | 112 |
| 5. | Residual combined fraction | 26.12 ± 2.30 | 24.05 ± 1.70 | 19.25 ± 0.74 | 23.48 ± 0.71 | 24.23 ± 1.60 | 21.29 ± 0.92 |

| | | Group II | | Group III | | | |
|---|---|---|---|---|---|---|---|
| NN 1 | Fractions 2 | 2 hours 9 | 3 hours 10 | background 11 | 1 hour 12 | 2 hours 13 | 3 hours 14 |
| 1. | Cholesterol esters | 23.59 ± 0.54 | 23.17 ± 0.46 | 22.49 ± 0.44 | 24.87 ± 0.54 | 24.43 ± 0.86 | 24.05 ± 0.62 |
| | % of variation | 102 | 100 | | 111 | 109 | 107 |
| 2. | Triglycerides | 17.73 ± 0.33 | 18.08 ± 0.56 | 19.36 ± 1.0 | 17.16 ± 0.48 | 17.29 ± 0.39 | 17.58 ± 0.84 |
| | % of variation | 106 | 108 | | 89 | 89 | 91 |
| 3. | Free fatty acids | 16.41 ± 0.67 | 17.38 ± 0.56 | 17.77 ± 0.65 | 17.77 ± 0.55 | 17.76 ± 0.36 | 15.05 ± 0.99 |
| | % of variation | 92 | 98 | | 100 | 100 | 85 |
| 4. | Cholesterol | 20.51 ± 0.55 | 20.88 ± 0.44 | 19.37 ± 0.35 | 19.39 ± 0.43 | 18.46 ± 0.79 | 17.34 ± 0.49 |
| | % of variation | 113 | 115 | | 100 | 95 | 90 |
| 5. | Residual combined fraction | 21.76 ± 0.46 | 20.49 ± 0.52 | 21.01 ± 0.61 | 20.81 ± 0.82 | 23.06 ± 1.10 | 25.90 ± 1.13 |

Group I - healthy europeoids,
Group II - healthy mongoloids,
Group III - alcoholism - suffering patients.

TABLE 21

Variation of the content of fractions of neutral lipoids in human blood serum of patients consumed a 40% solution of ethanol (in % of the total lipoids, M ± m) with the composition of this invention

| | | Group 1 | | | | Group II | |
|---|---|---|---|---|---|---|---|
| NN 1 | Fractions 2 | background 3 | 1 hour 4 | 2 hours 5 | 4 hours 6 | background 7 | 1 hour 8 |
| 1. | Cholesterol esters | 24.35 ± 2.04 | 23.91 ± 0.67 | 22.04 ± 0.41 | 21.53 ± 0.68 | 22.30 ± 1.01 | 24.32 ± 0.55 |
| | % of variation | | 98 | 91 | 88 | | 109 |
| 2. | Triglycerides | 16.41 ± 0.71 | 18.14 ± 0.30 | 18.48 ± 1.24 | 19.51 ± 0.69[1] | 19.95 ± 1.71 | 18.15 ± 0.55 |
| | % of variation | | 111 | 113 | 119 | | 91 |
| 3. | Free fatty acids | 15.96 ± 0.76 | 16.19 ± 0.57 | 16.30 ± 0.26 | 15.90 ± 0.24 | 16.12 ± 0.46 | 16.17 ± 1.10 |
| | % of variation | | 101 | 102 | 106 | | 100 |
| 4. | Cholesterol | 19.21 ± 0.86 | 18.87 ± 0.38 | 18.06 ± 0.84 | 20.06 ± 1.58 | 17.84 ± 0.28 | 18.02 ± 0.93 |
| | % of variation | | 98 | 94 | 104 | | 101 |
| 5. | Residual combined fraction | 24.07 ± 1.93 | 22.89 ± 0.55 | 24.52 ± 1.61 | 22.94 ± 1.17 | 23.79 ± 2.03 | 23.34 ± 0.60 |

| | | Group II | | Group III | | | |
|---|---|---|---|---|---|---|---|
| NN 1 | Fractions 2 | 2 hours 9 | 4 hours 10 | background 11 | 1 hour 12 | 2 hours 13 | 4 hours 14 |
| 1. | Cholesterol esters | 23.15 ± 1.45 | 22.89 ± 0.70 | 24.60 ± 0.59 | 24.05 ± 0.62 | 24.26 ± 0.34 | 22.94 ± 0.90 |
| | % of variation | 104 | 103 | | 100 | 101 | 95 |
| 2. | Triglycerides | 18.87 ± 2.11 | 19.47 ± 0.28 | 17.05 ± 0.52 | 16.50 ± 0.56 | 17.43 ± 0.49 | 18.77 ± 0.66 |
| | % of variation | 95 | 98 | | 97 | 102 | 110 |
| 3. | Free fatty acids | 15.83 ± 0.58 | 16.95 ± 0.84 | 15.95 ± 0.53 | 16.63 ± 0.41 | 17.00 ± 0.50 | 17.01 ± 0.52 |
| | % of variation | 98 | 105 | | 104 | 107 | 107 |
| 4. | Cholesterol | 17.66 ± 0.89 | 19.22 ± 0.45 | 18.37 ± 0.73 | 17.85 ± 0.44 | 19.07 ± 0.42 | 19.89 ± 0.49 |
| | % of variation | 99 | 108 | | 97 | 104 | 108 |
| 5. | Residual combined fraction | 24.46 ± 1.45 | 21.47 ± 1.33 | 24.03 ± 0.79 | 24.97 ± 1.08 | 22.24 ± 1.20 | 21.39 ± 0.51 |

[1] $p < 0.01$
Group 1 - healthy europeoids;
Group II - healthy mongoloids;
Group III - alcoholism-suffering patients.

TABLE 22

System ADG-ethanol, in patients consumed solutions of ethanol and composition of this invention

| | | | 40% ethanol | | | | 40% ethanol + composition of this invention | |
|---|---|---|---|---|---|---|---|---|
| NN 1 | | Fractions 2 | background 3 | 1 hour 4 | 2 hours 5 | 4 hours 6 | background 7 | 1 hour 8 |
| 1. | patients | ADG | 0.46 ± 0.16 | 1.24 ± 0.56 | 1.83 ± 0.58 | 2.39 ± 0.66 | 2.28 ± 0.68 | 3.56 ± 0.66 |
| 2. | | ethanol | 0 | 0.27 ± 0.01 | 0.198 ± 0.023 | 0.113 ± 0.014 | | 0.138 ± 0.032 |

TABLE 22-continued

| | | System ADG-ethanol, in patients consumed solutions of ethanol and composition of this invention | | | | | |
|---|---|---|---|---|---|---|---|
| 3. | mongoloids | ADG | 2.81 ± 0.97 | 3.15 ± 0.67 | 3.17 ± 0.87 | 3.15 ± 0.89 | 1.74 ± 0.32 | 1.69 ± 0.31 |
| 4. | | ethanol | 0.012 ± 0.007 | 0.174 ± 0.033 | 0.188 ± 0.024 | 0.064 ± 0.028 | 0 | 0.206 ± 0.023 |
| 5. | healthy | ADG | 2.90 ± 0.58 | 1.73 ± 0.29 | 3.04 ± 0.42 | 0.52 ± 0.28 | 2.56 ± 0.23 | 1.78 ± 0.68 |
| 6. | europeoids | ethanol | 0.023 ± 0.002 | 0.263 ± 0.028 | 0.0124 ± 0.013 | 0.035 ± 0.000035 | 0.049 ± 0.0004 | 0.174 ± 0.025 |

| | | | 40% ethanol + composition of this invention | | Composition of this invention | | | |
|---|---|---|---|---|---|---|---|---|
| NN | | Fractions | 2 hours | 4 hours | background | 1 hour | 2 hours | 4 hours |
| 1 | | 2 | 9 | 10 | 11 | 12 | 13 | 14 |
| 1. | patients | ADG | 1.85 ± 0.39 | 0.70 ± 0.25 | 1.06 ± 0.46 | 0.79 ± 0.27 | 1.79 ± 0.35 | 1.67 ± 0.47 |
| 2. | | ethanol | 0.182 ± 0.054 | 0.203 ± 0.022 | 0.04 ± 0.012 | 0.14 ± 0.014 | 0.076 ± 0.024 | 0.082 ± 0.018 |
| 3. | mongoloids | ADG | 2.34 ± 0.87 | 1.57 ± 0.31 | 2.48 ± 0.64 | 1.59 ± 0.58 | 1.69 ± 0.47 | 2.37 ± 0.76 |
| 4. | | ethanol | 0.105 ± 0.029 | 0.103 ± 0.033 | 0 | 0 | 0 | 0 |
| 5. | healthy | ADG | 2.35 ± 0.57 | 0.69 ± 0.34 | 1.00 ± 0.37 | 1.64 ± 0.40 | 1.37 ± 0.47 | 1.27 ± 0.36 |
| 6. | europeoids | ethanol | 0.174 ± 0.016 | 0.086 ± 0.01 | 0.006 ± 0.000008 | 0.042 ± 0.032 | 0.076 ± 0.035 | 0.015 ± 0.00004 |

Measurement units:
ADG (i/i); ethanol - mg %;
ADG - alcoholdehydrogenase

Under conditions of a double blank control the patients took 40% ethanol with the composition according to the present invention (1:50) or an aqueous solution of this composition. The volume of the taken liquid was 200 ml per 70 kg of the bodymass. The intervals between intakes were 4 days. Blood from vein was taken prior to the liquid intake, 1 hour, 2 and 4 hours thereafter for biochemical investigations. The test results are shown in Tables 17, 18, 19, 20, 21 and 22 hereinbelow.

We have also carried out for 10 months testing of the composition according to the present invention on 8,000 persons. To this end, alcoholic beverages containing the composition according to the present invention were used. The persons included in observations did not take any other alcoholic beverages during the entire period of tests. The total reduction of the alcohol consumption over the period of 10 months constituted 28.01%.

Within 10 months of tests the number of alcoholic psychoses in this group of persons reduced to four cases compared to 12.5 cases on the average over the preceding 6 similar periods.

The course of alcoholic intoxications has also changed: easier hang-over states, a lowered demand for a hang-over drink due to the appearance of somatic complaints inhibiting continuation of heavy-drinking periods in alcohol-abusing persons.

No demographic and social excesses were noted among persons included in observations.

Therefore, on the ground of the studies and experiments conducted a conclusion may be made that the general effect of the composition according to the present invention directed against negative after-effects of the alcohol consumption is composed of the effects provided by the composition ingredients on the maim biological signs of alcohol:

membranotropic effect of ethanol is lowered due to normalization of the membrane stability owing to regulation of the synthesis of cholesterol, its esterification and inclusion into the structure of membranes. This also results in normalization of activity of membrane-combined enzymes and other permeability characteristics according to the principle of Vitamin P—activity;

oxidation of ethanol is effected mainly in the liver with exhaustion of the oxidized form of nicotinamidedinucleotide $NAD^+$. Other oxidizing processes occurring with the use of $NAD^+$ are inhibited. The ingredients of the composition according to the present invention act as hydrogen ion acceptors and contribute to lowering of the ratio $NADH/NAD^+$;

in the cousre of oxidation of ethanol in the organism the most toxic metabolite—acetaldehyde- is formed which when present in tissues is responsible for toxicological and narcotic characteristics of ethanol. The rate of oxidation of ethanol and acetaldehyde depends first of all on activity of alcoholdehydrogenase and acetaldehydedehydrogenase. The ingredients of the composition according to the present invention are capable of lowering the activity of alcoholdehydrogenase by decelarting oxidation of ethanol and, furthermore, of entering into competitive relations with ethanol as a substrate for alcoholdehydrogenase. In doing so, due to conformation of alcoholdehydrogenase there is effected oxidation of not ethanol, but, first of all, of the competiting substrate incorporated in the composition according to the present invention;

calorigenic effect of ethanol, owing to which it is a successful competitor in respect of other sources of energy while being superior to them in the availability criterion. This causes the narrowing of the main metabolic chain of conversion of a number of edible substances due to a competitive alienation of specific dehydrogenases and their prostetic groups. The composition according to the present invention contributes to conservation and, upon a long-time consumption of alcohol, to restoration of other energy supply routs, in particular through gluconeogenesis.

The carried out tests of the composition according to the present invention in experiments on animals, in observation on volunteers have shown that the composition of this invention has an ability of providing rational ways for a high resistance and recovery of the organism. In all cases of extremal loads on animals (of both physical, chemical and biological character) a clearly-pronounced stress-protecting effect is observed. In addition thereto, the composition according to the present invention has specific biological properties of inhibiting the formation of a physical dependence on alcohol and of lowering detrimental effects of its toxic metabolites.

A wide range of a biological action of the composition according to the present invention is explained by the fact that it comprises an indispensible set of substrates ensuring optimal ways of metabolism directed to the preservation of energy resources of the organism by way of synthesis of carbohydrates from non-carbohydrate metabolites through gluconeogenesis.

EXAMPLE 1

A composition contains the following ingredients, mg/g: leukodolphinidine 120, leukocyanidine—80, leukopelargonidine—45, (—)epigallocatechin—42, (±)gallocatechin—31, (—)epicatechin—29, (+)catechin—60, (—)epicatechingallate—18, kaempferol-3-monoglucoside—17, quercetin-3-monoglucoside—22, myricetin-3-monoglucoside—14, quercetin-3-glucoside—24, astragalin—13, lignin—75, D-glucose 83.6, D-fructose—64, saccharose—33,5, raffinose—24, arabinose—25, xylose—31.6, pectine—20, lysine—3.4, histidine—0.2, arginine—0.4, aspartic acid—4.3, threonine—1.1, serine—2.0, glutamic acid—3.0, proline—3.3, glycine—2.2, alanine—3.8, cystine—0.3, valine—1.8, methionine—0.4, isoleucine—0.8, leucine—2.8, tyrosine—0.5, phenylalanine—0.3, tartaric acid—4.2, malic acid—3.8, citric acid—4.0, ascorbic acid—4.0, α-ketoglutaric acid—1.9, fumaric acid—2.1, galacturonic acid—2.2, glyceric acid—1.8, glycolic acid—1.7, glycouronic acid-3.0, oxalic acid—2.3, succinic acid—5.0, shikimic acid—3.0, α-amyrine—0.4, β-amyrine—0.4, loupeol—0.3, taraxasterol—0.4, taraxerol—0.4, germanicol—0.3, obtusifoliol—0.8, citrostadienol—0.7, β-cetosterine—3.2, stigmasterol—1.0, kaempesterol—0.8, oxymatairesinol—2.9, matairesinol—2.3, pinoresinol—2.5, liovyl—2.7, isolariciresinol—2.7, olivyl—1.9, querinol arabinoside—6.2, querinol xyloside—3.8, paraoxybenzoic acid—1.2, protocatechinic acid—3.5, gallic acid—1.9, vanillic acid—4.3, syringe acid—4.1, vanilline—1.5, syringe aldehyde—1.3, sinapic aldehyde—0.9, coniferyl aldehyde—1.3, cotadecanolferulate—1.5, eicosanolferulate—1.4, docosanolferulate 1.1, tetracosanolferulate—0.5, hexacosanolferulate—0.5.

This composition in the amount of 5 g is dissolved in 100 ml of a 40% aqueous-alcoholic solution.

The resulting aqueous-alcoholic solution has a red-brown colour, a weak characteristic scent and a soft astringent taste. The solution has a low toxicity. The $LD_{50}$ is 36.5 ml/1,000 g of bodymass of a rat. The solution is capable of providing rational ways for resistance and recovery of the organism, suppresses the formation of a physical dependence on alcohol and lowers detrimental effects of its toxic metabolites.

EXAMPLE 2

A composition contains the ingredients similar to those sepcified in Example 1 in the following amounts, mg/g: leukoanthocyanes—197.1, catechins—137.7, flavanols—72.9, lignin—61.2, reducing sugars—410.76, pectin—16.2, free aminoacids—24.3, organic acids—32.4, sterols, methylsterols, dimethylsterols—1.78, lignans—12.1, lignan glycosides—8.1, phenolic acids—12.1, phenolic aldehydes—4.05, alkylferulates—4.05.

This composition in the amount of 5 g is dissolved in 100 ml of a 40% aqueous-alcoholic solution. The resulting aqueous-alcoholic solution has a red-brown colour, a weak specific scent and a soft slightly sweet astringent taste. The solution has a low toxicity: the $LD_{50}$ is 41.2 ml/1,000 g of bodymass of a rat.

The solution has an ability of ensuring rational ways for resistance and recovery of the organism, it slightly inhibits the formation of a physical dependence on alcohol and reduces, to a certain extent, negative effects of its toxic metabolites; the composition has a low activity which is even not recorded in a number of biological tests.

EXAMPLE 3

A composition contains the ingredients similar to those specified in Example 1 hereinbefore in the following amounts, mg/g: leukoanthocyanes—219, catechins—153, flavanols—81, lignin—68, reducing sugars—345.17, pectin—18, free aminoacids—27, organic acids—36, sterols—4.5, methylsterols—1.35, dimethylsterols—1.98, lignans—13.5, lignan glycosides—9, phenolic acids—13.5, phenolic aldehydes—4.5, alkylferulates—4.5.

This composition in the amount of 5 g is dissolved in 100 ml of a 40% aqueous-alcoholic solution. The resulting solution is of a red-brown colour, it has a weak specific scent and a soft astringent taste. The solution has a low toxicity: its $LD_{50}$ is 36.5 ml/1,000 g of bodymass of a rat.

The solution is capable of providing rational ways for resistance and recovery of the organism; it inhibits the formation of a physical dependence on alcohol and slightly lowers negative effects of its toxic metabolites.

EXAMPLE 4

A composition contains the ingredients similar to those specified in Example 1 hereinbefore in the following amounts, mg/g: leukoanthocyanes—270, catechins—187, flavanols—99, lignin—83, reducing sugars—197.5, pectin—22, free aminoacids—33, organic acids—44, sterols—5.5, methylsterols—1.65, dimethylsterols—2.42, lignans—16.5, lignan glycosides—11, phenolic acids—16.5, phenolic aldehydes—5.5, alkylferulates—5.5.

This composition in the amount of 5 g is dissolved in 100 ml of a 40% aqueous-alcoholic solution. The resulting solution has a red-brown colour, a weak specific scent and a soft astringent taste. The solution is of a low toxicity: its $LD_{50}$ is 36.5 ml/1000 g of bodymass of a rat.

The solutions is capable of ensuring rational ways for resistance and recovery of the organism, inhibits the formation of a physical dependence on alcohol and lowers negative effects of its toxic metabolites.

EXAMPLE 5

A composition contains the ingredients similar to those of Example 1 in the following amounts, mg/g: leukoanthocyanes—297, catechins—205, flavanols-109, lignin—91, reducing sugars—120.6, pectin-24, free aminoacids—36, organic acids—48, sterols—6, methylsterols—1.8, dimethylsterols-2,6, lignans—18, lignan glycosides—12, phenolic acids—18, phenolic aldehydes—6, alkylferulates—6.

This composition in the amount of 5 g is dissolved in 100 ml of a 40% aqueous-alcoholic solution. The resulting solution has a red-brown colour, a pronounced specific odour and an astringent taste. The solution has a low toxicity: its $LD_{50}$ is 33.3 ml/1,000 g of bodymass of a rat.

The solution is capable of ensuring rational ways for resistance and recovery of the organism; it inhibits the formation of a physical dependence on alcohol and diminishes detrimental effects of its toxic metabolites.

What is claimed is:

1. A composition inhibiting the development of a pathological addiction to alcohol and having a stress-protecting effect which comprises the following ingredients, mg/g:

| | |
|---|---|
| leukoanthocyanes | 219–270 |
| catechins | 153–187 |
| flavonols | 81–99 |
| lignin | 68–83 |
| reducing sugars | 216–264 |
| pectin | 18–22 |
| organic acids | 76.5–93.5 |
| sterols | 4.5–5.5 |
| methylsterols | 1.35–1.65 |
| dimethylsterols | 1.98–2.42 |
| lignans | 13.5–16.5 |
| lignan glycosides | 9–11 |
| phenolic aldehydes | 4.5–5.5 |
| alkylferulates | 4.5–5.5. |

2. An alcoholic beverage containing an addiction-inhibiting amount of the composition of claim 1.

3. An alcoholic beverage containing about 40 percent ethanol and about 5 percent by weight of the composition of claim 1.

4. A method for inhibiting the development of a pathological addition to alcohol in a subject, which comprises administering to said subject, an addiction-inhibiting amount of the composition of claim 1.

5. The method of claim 4 wherein said composition is contained in an alcoholic beverage.

6. The method of claim 4 wherein said subject is a human being.

7. The composition of claim 1 wherein said organic acids contain 27–33 mg of free aminoacids.

8. The composition of claim 1 wherein said organic acids contain 13.5–16.5 mg of phenolic acid.

9. The composition of claim 1 wherein said organic acids contain 36–44 mg of at least one acid selected from the group consisting of tartaric acid, malic acid, citric acid, ascorbic acid, α-ketoglutaric acid, fumaric acid, galacturonic acid, glyceric acid, glycolic acid, glycouronic acid, oxalic acid, succinic acid and shikimic acid.

* * * * *